United States Patent [19]

Sommers

[11] 4,382,445
[45] May 10, 1983

[54] PHYSIOLOGICAL FLUID SHUNT SYSTEM AND IMPROVEMENTS THEREFOR

[75] Inventor: Michael W. Sommers, Chicago, Ill.

[73] Assignee: Cosmos Research Associates, Elgin, Ill.

[21] Appl. No.: 212,987

[22] Filed: Dec. 4, 1980

[51] Int. Cl.³ .............................................. A61M 25/00
[52] U.S. Cl. ......................................................... 604/8
[58] Field of Search ................ 128/348, 350 R, 350 V

[56] References Cited

U.S. PATENT DOCUMENTS

| | | | |
|---|---|---|---|
| 3,492,996 | 2/1970 | Fountain | 128/350 V |
| 3,623,484 | 11/1971 | Schulte | 128/350 R |
| 3,654,932 | 4/1972 | Newkirk et al. | 128/350 V |
| 3,674,033 | 7/1972 | Powers | 128/350 R |

Primary Examiner—Dalton L. Truluck
Attorney, Agent, or Firm—Edward D. Gilhooly

[57] ABSTRACT

Comprehensive shunting systems for draining fluid from a region of the body, such as in the treatment of hydrocephalus. The shunting systems greatly improve the drainage of such fluid and are capable of attaining a significantly extended lifetime of service within the patient being treated. A catheter accommodates the growth of the patient, even when the shunt system is inserted within an infant. The shunt systems improve drainage of fluid through a shunt by preventing proteinaceous buildup resulting in shunt malfunction. In addition, an improved proximal catheter is disclosed which is capable of being caused to assume a position spaced from the body tissue, i.e., ventricular lining. Valve assemblies attain pressure regulation, such that stagnant reservoirs or columns of fluid are eliminated to prevent formation of sediment and ultimately valve malfunction, and collapse of a body cavity due to evacuation of fluid is not encountered. A trocar for inserting the catheter into the body for ease of the patient and surgeon. A syphon effect within the shunt system is also prevented and a variable pressure response of a slit valve at the time of surgery is provided.

4 Claims, 22 Drawing Figures

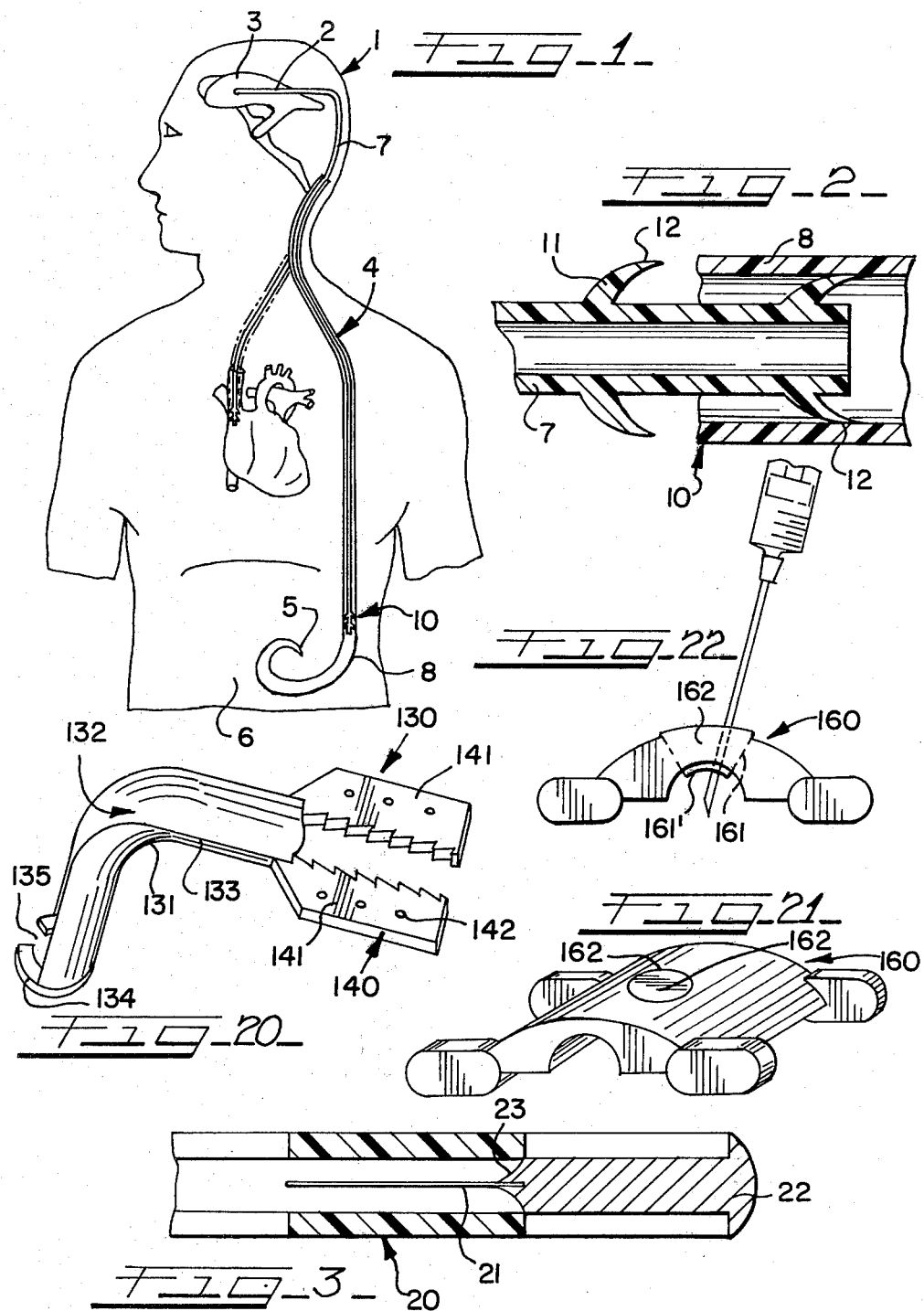

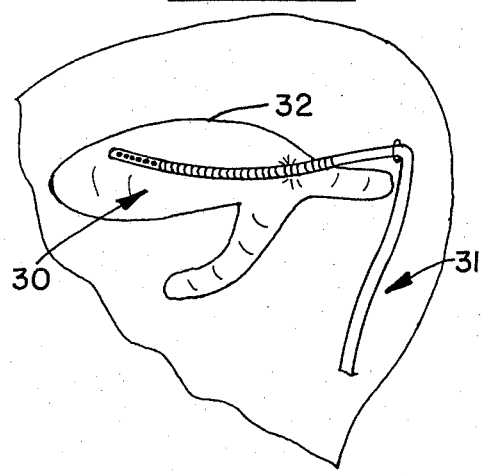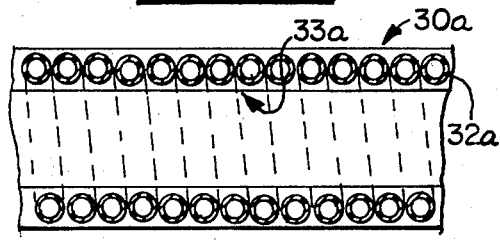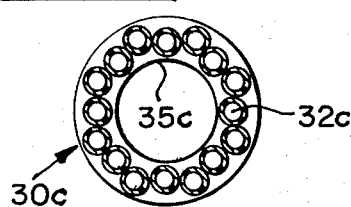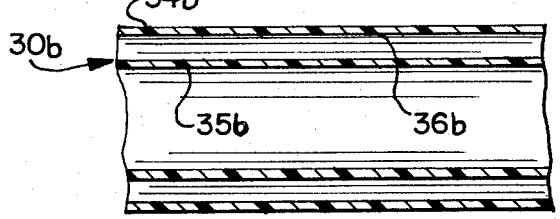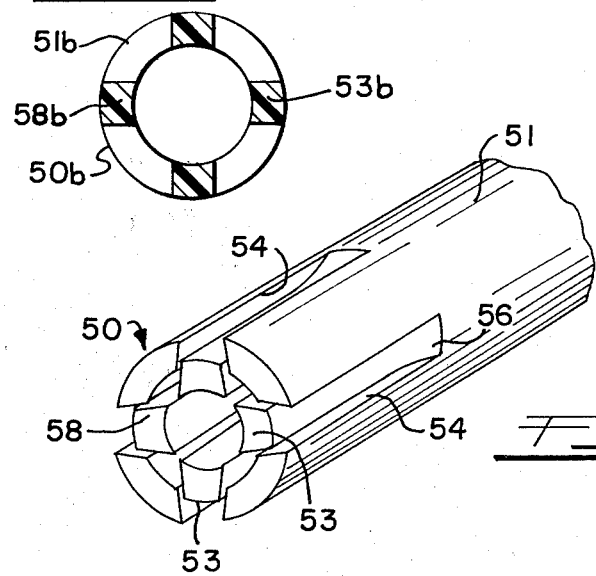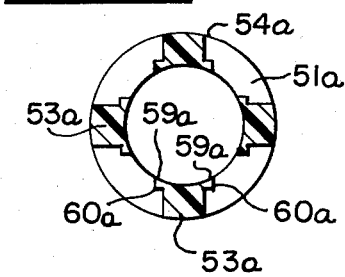

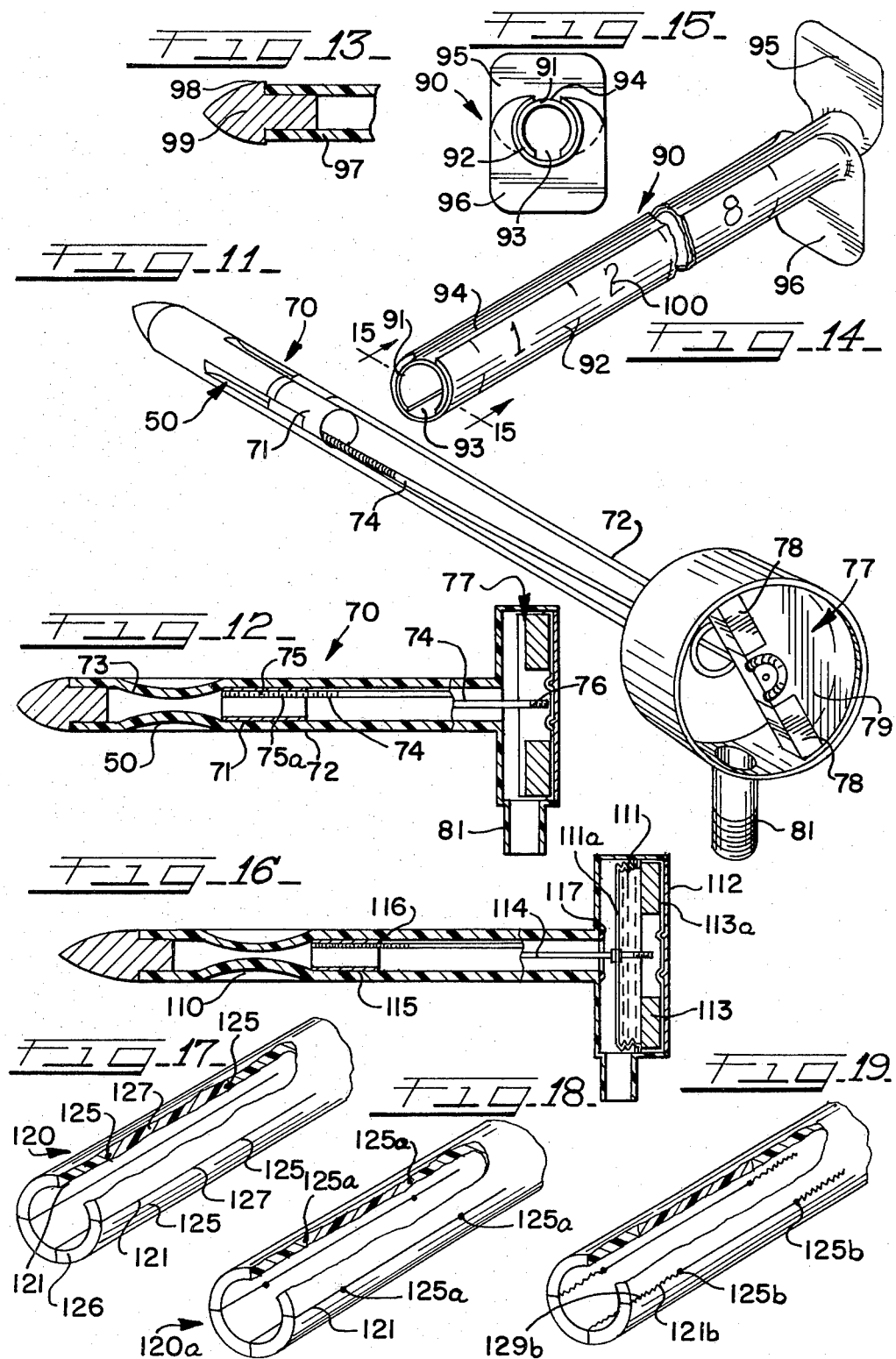

PHYSIOLOGICAL FLUID SHUNT SYSTEM AND IMPROVEMENTS THEREFOR

BACKGROUND OF THE INVENTION

This invention relates in general to drainage of fluid from within the human body and, in particular, to a catheter system to drain fluid from cavities of the body.

More specifically, but without restriction to the particular use which is shown and described, this invention relates to an improved shunt system by which fluid may be effectively drained to reduce fluid pressure and fluid volume in a body cavity, such as in the ventricles of the brain.

Typically, numerous types of catheter systems are employed to drain fluid which accummulates in various regions of the human body. A particularly well known use of such a catheter system is found in the treatment of a condition known as hydrocephalus. The term hydrocephalus generally refers to a physiological entity in which fluid tends to accummulate within one or more compartments of the brain. The presence of such excess fluid and pressure within the brain area of a human can lead to serious medical problems for the individual, if the symptoms of hydrocephalus are not treated. Generally, various techniques have been relied upon to relieve the presence of excess fluid and pressure build-up within the central nervous system as occurs in this disease. The use of the catheter drainage systems has in the past been helpful in this treatment, and is well founded.

The first recorded attempt at mechanically shunting hydrocephalus is generally considered to have occurred in 1898. Since that time, many different methods of allievating the symptoms of hydrocephalus have been attempted. It was not until the early 1950's that mechanical shunts achieved any significant degree of success in controlling hydrocephalus. In its simplest form, a shunt is merely a fluid control system having a proximal catheter inserted into a lateral ventricle of the brain, or such area where fluid build-up occurs, and a shunt or conduit system extending downward from that area into a lower region of the body for disposition of CSF. Generally, a shunt system terminates at a distal end at a point where the body may readily dispose of the fluid that is drained through the system, such as, within the abdominal cavity or into a vein of the heart in some cases.

Many variations of the basic shunt design have been attempted in order to improve the hydrodynamics and reliability of shunts. Nevertheless, known shunt systems continue to be subjected to numerous deficiencies in performance and reliability which arise during their use in the human body. For example, with the implantation of any shunt system, be it ventricular-peritoneal, ventricular-artrial, or the like, the device must have the capability to accommodate growth in patients who have not reached adulthood. A current practice is to pass an additional amount of catheter into the distal receptor site so that, at least theoretically, the shunt can "grow" with the patient and not require replacement or modification due to insufficient length. It has also been attempted in the prior art to provide a system having a packet of coiled distal catheter inside the chest so that it might uncoil as the patient grows. Another attempt at achieving growth capability in a shunt system is disclosed in U.S. Pat. No. 3,623,484 to Schulte. The system shown in the Schulte patent, however, has not proved clinically successful, since it only provides an elongation of two inches in a patient and has not provided practical.

In another problem posed by known shunt systems, the sedimentation of protein and debris in cerebrospinal fluid tends to plug the valve at the distal or proximal end of the shunt system. For example, such an accumulation of sedimentation occurs in one particular known shunt system, because there exists a dead space of approximately two millimeters between the distal end valve slits and the distal end plug or between the proximal end and the fenestrations. It is within this dead space that debris builds up to the point where it interferes with proper shunt operation and hence, prevents suitable drainage of fluid from the ventricle. This is known as a malfunction.

Ever since the first practical shunts were placed in the lateral ventricle, the problem of encroachment by body tissues into the inlet fenestrations has been recognized. This tissue invasion, most notably by the choroid plexus, is one of the major causes of proximal end related malfunctions. Many techniques have been employed to physically separate the catheter from the choroid plexus and/or ependymal lining. Such restraining systems are disclosed in U.S. Pat. No. 3,419,010 to Williamson; U.S. Pat. No. 3,516,410 to Hakim; U.S. Pat. No. 3,626,950 to Schulte; and U.S. Pat. No. 3,669,116 to Heyer. Unfortunately, none of the foregoing techniques of maintaining the catheter in spaced relationship to the walls have been successful, and encroachment by body tissue inherently occurs.

The regulation of intercranial pressure in the shunting of fluid in hydrocephalic patients has also presented difficulties in the use of prior catheter systems. In the prior art, regulation of pressure is accomplished typically by two distinct techniques. A common device for pressure regulation involves a valve placed in the shunt line at a level slightly below the occipital horn of the lateral ventricle. The other common type of system utilizes a valving mechanism situated at the outlet of the catheter at its distal end, such as within the abdomen. The actual construction of such regulatory valves previously employed has varied enormously from system to system. However, the slit-type valve is generally a commonly used form in popular shunts, such as in a typical one piece system. The slit valve is a simple device positioned at the distal end, in which the edges of the slit expand apart when internal pressure exceeds a predetermined value, to allow the buildup of fluid within the ventricle to pass until the pressure decreases, and the edges once again approximate. An advantage of this type of valve is that it acts as a one way valve, and a greater pressure on the outside only serves to close the valve. One example of a typical slit valve disposed at the distal end is disclosed in U.S. Pat. No. 3,111,125 to Schulte. However, there are advantages for valve usage at the proximal end to control pressure. At the proximal end, no stagnant reservoir or column of cerebrospintal fluid is created which could include sediment and cause valve malfunction.

The management of hydrocephalus is also at times complicated by patients having large ventricles. When such large ventricles are shunted, a risk of collapsed ventricles is present, because of the decreased pressure that can ultimately result in subdural fluid collections, due to tearing of the cortical mantle away from its covering. This consideration often greatly complicates the overall effective management of the patient having hydrocephalus. Experimental studies have shown that a simple shunt is not perfectly addressed to the hydrodynamic needs of the patient with severe hydrocephalus. Animal studies have shown that to obtain proper rebounce of cerebral mantle thickness, a lower interventricular pressure must be established to allow for the rebounce followed by a subsequent slight increase within the normal pressure range.

In the patient with either an unusually high pressure or large ventricles and a closed intercranial space, the advantage of a variable pressure valve becomes important. Modifications to shunts so that flow can be terminated have been made previously in attempts to lessen the rapid decompression of the interventricular space when desired. However, the deficiencies of such prior "on-off" shunts are well known in the art.

Other shortcomings are associated with the use of conventional treatments of hydrocephalus. In the surgical treatment of a patient with this disease, the insertion of a ventricular catheter through the cerebral mantle and into the ventricle requires a rigid support guide, because the catheter itself is too flexible. Various shunt systems known in the prior art employ different methods to pass the catheter. One of the more prevalent techniques is to pass a trocar into the ventricle, remove the center, and then pass the proximal catheter down the trocar housing. A disadvantage of this type of trocar is its large diameter and thusly, unnecessary impact to the brain tissue as it is passed through the cortex.

In still another problem presented by known shunt systems, the complication of a column of liquid existing between the inlet and the outlet of the catheter poses a potential problem associated with the siphon effect as the patient changes position in normal activity. Prior attempts to resolve this problem have not been satisfactory in allieviating this difficulty.

Known shunt systems demonstrate other inadequacies while treating hydrocephalus. The valve located in the distal end of the popular shunt system, in the form of a single piece unit, includes several slits which are displaced outward when the pressure within the shunt reaches a given level as previously discussed. At the present time, slit type valve shunts are generally provided in three pressure ranges, high, medium and low. In most cases, the major difference in these shunts is simply the length of the slit valve, i.e., the longer the slit, the lower the resultant opening pressure will be. However, none of the slit valves heretofore allow ready adjustment to modify the pressure ranges at the time of insertion or post-insertion.

The attachment of shunt tubing to appropriate parts of the body has presented many problems. For example, the clips employed to secure the shunts in place in the past have been bulky and inconvenient to secure at surgery. In addition, prior clips have not provided access to the interior of the shunt system as needed during use.

As has been discussed, known techniques of shunting the cerebrospinal fluid from a cavity, such as the ventricle, are associated with numerous deficiencies which interfere with the effectiveness of treatment of a patient which requires the reduction of pressure and volume of fluid from a region of the body.

SUMMARY OF THE INVENTION

It is, therefore, an object of this invention to improve systems for draining fluid from a region of the body.

Another object of this invention is to improve the treatment of hydrocephalus.

A further object of this invention is to improve the capability of a fluid shunt system in accommodating the growth of the human in which it is implanted.

Still another object of this invention is to prevent malfunctions of the valve at the distal or proximal end of a shunt system.

A still further object of this invention is to suspend, by buoyancy, the catheter inserted into the cavity of the body, such as the ventricle.

Still another object of this invention is to improve pressure regulation within a shunt system for draining fluid from a body cavity.

A still further object of this invention is to prevent the collapse of the cavity being shunted by a catheter.

Still another object of this invention is to improve the surgical insertion of a ventricular catheter through the cerebral mantle and abdominal wall of a human.

A still further object of this invention is to prevent a syphon effect within the shunt system implanted in a human.

Still another object of this invention is to permit a slit valve of a shunt system to be adjusted for a selected pressure response at the time of insertion at surgery.

A further object of this invention is to improve the shunt clip used to secure the shunt in place.

Another object of the invention is to permit withdrawal of a quantity of fluid from the shunt.

These and other objects are attained in accordance with the present invention wherein there is provided comprehensive shunting systems and improvements thereof for draining fluid from a region of the body, such as in the treatment of hydrocephalus. The systems of the invention greatly improve the drainage of such fluid and are capable of attaining a significantly extended lifetime of service within the patient being treated. The catheter of the invention includes means to accommodate or adapt to the growth of the patient, even when the shunt system is inserted within an infant. The shunt systems herein disclosed greatly improve drainage of fluid through a shunt by preventing proteinaceous buildup resulting in shunt malfunction. In addition, an improved proximal catheter is disclosed which is capable of being caused to assume a position spaced from the body tissue, i.e., ventricular lining. Moreover, the invention of the application achieves greater improved pressure regulation, such that stagnant reservoirs or columns of fluid are eliminated to prevent formation of sediment and ultimately valve malfunction. The system of the invention further includes improved valve means by which collapse of a body cavity due to evacuation of fluid is not encountered as in the prior art. Moreover, the system of the invention includes means to allow the catheter to be inserted into the body in an improved manner for the benefit of the patient and surgeon. In addition to the foregoing advantages, the systems of the invention further prevents the occurrence of a syphon effect within the shunt system and includes a better means for regulating the pressure response of the valve of the system at the time of surgery. Moreover, there is disclosed an improved and less bulky shunt clip as well as means to permit fluid to be removed from a shunt catheter. Accordingly, the shunt system of the invention includes various improved means by which a region of the body may be effectively drained in a superior manner, such as needed in the treatment of hydrocephalus.

DESCRIPTION OF THE DRAWINGS

Further objects of the invention together with additional features contributing thereto and advantages accruing therefrom will be apparent from the following description of preferred embodiments of the invention which are shown in the accompanying drawings with like reference numerals indicating corresponding parts throughout, wherein:

FIG. 1 is a front schematic view of the shunt system of the invention having provision to accommodate growth of the patient;

FIG. 2 is a partial sectional view of the telescoping catheters of the invention accommodating growth in the system of FIG. 1;

FIG. 3 is a sectional view of an improved end plug of the invention for use in a one piece shunt system;

FIG. 4 is a perspective side view of a buoyancy catheter of the invention positioned in the lateral ventricle of a human brain in connection with a shunt system;

FIG. 5 is a partial cross-sectional view of one embodiment of the buoyancy catheter as shown in FIG. 4;

FIG. 6 is a side partial sectional view of another embodiment of the buoyancy catheter of FIG. 4;

FIG. 7 is an end cross-sectional view of still another embodiment of the buoyancy catheter of FIG. 4;

FIG. 8 is a perspective view in section of a proximal end parallel slit valve of the invention for use in a shunt system;

FIG. 9 is an end sectional view of another embodiment of the proximal end parallel slit valve of the invention;

FIG. 10 is an end sectional view of still another embodiment of the proximal end parallel slit valve of the invention;

FIG. 11 is a side perspective view of a variable pressure proximal valve of the invention for use in a shunt system;

FIG. 12 is a side sectional illustration of the variable pressure valve of FIG. 11;

FIG. 13 is a partial sectional view of an end plug of the modification for the plastic shunt insertion trocar;

FIG. 14 is a schematic illustration of a plastic shunt insertion trocar of the invention for inserting a shunt catheter;

FIG. 15 is an end sectional view of the trocar of FIG. 14;

FIG. 16 is a side sectional view of an anti-syphon chamber of the invention;

FIG. 17 is a perspective view with parts in section of a first embodiment of a reducible pressure slit valve of the invention for a shunt system;

FIG. 18 is a perspective view with parts in section of a second embodiment of a reducible pressure slit valve of the invention for a shunt system;

FIG. 19 is a perspective view of a third embodiment of a reducible pressure slit valve of the invention for a shunt system of the invention;

FIG. 20 is a perspective view of a neonatal proximal shunt clip of the invention;

FIG. 21 is a perspective view of an access port shunt of the invention; and

FIG. 22 is an end view with parts broken away of a neonatal proximal shunt clip of FIG. 21.

DESCRIPTION OF THE PREFERRED EMBODIMENTS

Referring now to FIGS. 1 and 2, there is illustrated one embodiment of a shunt system of the invention implanted with a human body. The shunt system, generally designated by reference numeral 1, includes an upper proximal catheter 2 which is implanted in the ventricular system 3 of the brain to drain fluid and reduce the pressure which accumulates in this region of the body. The shunt system 1 includes a tube or conduit 4 which extends downward to terminate at distal end 5 in the abdominal region 6 where the fluid being drained from the ventricular system may be absorbed by the body. Alternatively, the distal end may be extended into atrium portion 6a of the heart as shown in phantom in FIG. 1. The conduit 4 comprises a two sectional catheter having an upper tubular portion 7 and a lower tubular portion 8, one of which portion fits within the other. Although either portion 7 or 8 may be the inner component, the upper portion 7 is shown in FIG. 1 within lower portion 8. The lower end 9 of portion 7 may extend within tube 8 down to the distal end 5 to permit relative movement between the sections 7 and 8 as the patient grows, such as, for example, from infancy to childhood, infancy to adulthood, various stages of childhood to adulthood and the like. Since the ends of the conduit are secured to the patient, his or her growth applies a tensile force to the shunt 1 to cause such relative movement between the sections.

As shown in FIG. 1, the internal flow path within tube 4 is maintained in a sealed realtionship, by the presence of a flange section 10, despite relative movement of the tube sections 7 and 8. The flange section 10 includes one or more continuous, flexible flange gaskets 11 integrally formed on the inner catheter portion 7. The purpose of the flange or flanges is to not only maintain a fluid-tight seal between the outer region 12 of gaskets 11, but also to serve as a slight impediment to telescoping in the opposite direction due to the tilting orientation of the gaskets 11. The flange gasket 11 can be placed on either catheter 7 or 8 depending on the relative motion of the catheter to the cerebrospinal fluid pressure. The wall to wall spacing between catheters 7 and 8, as well as the length and number of flanges 11 required, are interdependent. The diameter of the one or more flanges 11 is slightly larger than the inside diameter of the outer catheter and is so constructed that it deflects in the manner shown in FIG. 2 to inhibit movement of the section 7 in the direction of tilting. In conjunction with the use of the growth catheter herein disclosed, spurs of material (not shown), which flex to allow proper movement of the catheter, but not in the wrong direction, may be placed upon the end of the proximal catheter 2. Such spurs, acting as a stop in one direction, could prevent possible migration of the catheter to an unwanted area, if disconnection occurs.

In the catheter system 1 shown in FIG. 1, radioopaque markers (not shown) can be placed on the ends of both catheter sections 7 and 8, so that radiological examination can determine the "growth" of the catheter. In addition, the outside surface of the inner catheter 7 can be treated with a material to promote easy slippage of the catheters inside one another. It is also advantageous in certain situations to place an inward biased flange on the inner surface of the outer catheter at the proximal end. Such a flange (not shown) would have the function of preventing body material from invading the space between the catheters 7 and 8 and possibly restricting free movement.

Referring now to FIG. 3, there is illustrated an embodiment of an improved end plug of the invention for use in various shunt systems, such as the one piece shunt system currently in use throughout the world. In the slit valve 20 having a plurality of elongated slits 21 as shown in FIG. 3, which is positioned at the distal end of the shunt system, the end plug 22 of the invention is provided with a central section filling the distal end up to a position adjacent to the edge of the slits 21 of the valve. Such a longer end plug does not interfere with the normal operation or presure sensitivity of the valve 20, but rather acts as a means to decrease shunt malfunctions due to distal end plugging caused by proteinaceous build-up and other sedimentation and debris in the dead spot between the slit and the plug. A similar type plug (not shown) for the proximal end can also be incorporated to eliminate the dead space between that current end plug and the opening fenestrations of the catheter.

Referring now to FIG. 4, there is illustrated a buoyancy proximal catheter 30 in accordance with the invention inserted within the lateral ventricle 32 of the brain in such a manner that the proximal catheter remains in s spaced relationship to the ventricular wall. The catheter 30 may be employed with any conventional shunt system, and is not limited to shunting of cerebrospinal fluid. The buoyancy catheter 30, in fact, can be used for any medical use in which the patency of such a catheter would be enhanced by its separation from body tissue. The catheter is inserted into the ventricle in the conventional manner, but the proximal end includes buoyancy means, as will be described, to suspend the proximal end within the ventricle by being made either zero or positively buoyant.

Referring to FIG. 5, one technique of the invention for achieving flotation of the proximal end catheter attached to a shunt system 31 is shown. The proximal end catheter 30a of FIG. 5 may be suspended for flotation in a manner such that the outside diameter of the proximal catheter is not altered as compared to the prior catheters. This is accomplished by the provision of a tubing 32a wrapped around the internal diameter 33a of the catheter and within the catheter outer wall. By replacing a portion of the shunt wall with such hollow tubing, a desired degree of flotation is achieved. The tubing 32a used may be of any thin walled material to entrap air or gas to provide a selected buoyancy in conjunction with the spacing of the tubing 32a and amount of shunt material replaced. To insure patency of the contained air or flotation gas, seals (not shown) may be provided along the length of the buoyancy tubing 32a to minimize the possibility of loss of flotation.

Referring now to FIG. 6, there is illustrated another embodiment of the buoyancy proximal end catheter of the invention, generally designated as catheter 30b. In the embodiment of FIG. 6, flotation is created by a thin wall flotation envelope 34b entrapping air or gas defined by inner wall 35b and outer wall 36b and which envelope is a fabricated part of the proximal catheter 30b itself. The envelope 34b would have a smaller wall surface area and thus, would have a greater buoyancy than the tubing 32a shown in FIG. 5.

Referring to FIG. 7, there is shown still another embodiment of the flotation technique to suspend a catheter 30c within a ventricle or other regions of the body having fluid therein. The flotation tubing 30c of FIG. 7 comprises a plurality of parallel tubes 32c arranged about the inner wall 35c of the catheter. The tubes extend parallel to the axis of the catheter for a length sufficient to suspend the member as shown in FIG. 4.

It should be apparent that flotation of the catheter 30 as shown in FIG. 4 could be achieved by use of small flotation sections or flotation tubes (not shown) formed into rings. These flotation rings would attain the desired individual flotation characteristics by being stacked along the proximal end of the catheter and then integrally formed as part of the shunt. In addition, the catheter may be constructed as a cellular material having air cells within the catheter wall or having a foam material forming at least a portion of the wall. The various embodiments of a buoyant proximal end catheter 30 may be used in any type of shunt system other than the specific shunt systems disclosed herein. The concept of a buoyancy catheter according to the invention is also not limited to the shunting cerebrospinal fluid, but rather is applicable to any medical use in which the patency of such a catheter would be enhanced by its separation from body tissues provided by the buoyancy effect.

Referring now to FIG. 8, there is illustrated a parallel valve 50 of the invention for the proximal end shunting catheter. The parallel slit valve 50 acts to regulate intercranial pressure by being responsive to the build-up of ventricular CSF pressure. The parallel slit valve of the invention is generally positioned at the proximal end of the catheter 51 and includes a plurality of diaphram-like members 53 which are shown in deflected position in FIG. 8 due to external pressure. The diaphrams 53 are disposed in elongated slots 54 of the catheter 51, and each end 56 of the diaphrams 53 (one of which is shown in FIG. 8) is integrally coupled to the catheter 51. Obviously, the diaphrams 53, which are shown as four in number, are deflected in a distorted manner in response to external pressure as illustrated in FIG. 8 and act to create a variable flow area through the slots 54 and into the catheter for drainage. Although four diaphrams are shown, other numbers of diaphram(s) can be employed.

To accomplish the function of stretching inward in response to external pressure, the diaphragms 53 are constructed from a more pliable material than the material of the catheter 51 surrounding the diaphram. This insures that the diaphrams 53 are deflected by fluid as opposed to the catheter material. In the embodiment of FIG. 8, the cross-sectional shape 58 of the diaphrams 53 of the proximal parallel valves is slightly wedge-shaped or acutely angled to prevent outward movement beyond the peripheral outer wall of the catheter 51 and thus allows only uni-directional flow from the exterior of the catheter to its interior.

In FIG. 10, there is illustrated another embodiment of the parallel slit valve of the invention for the proximal end catheter in which a modified cross-sectional shape of diaphrams 53a is shown. The slots 54a of the catheter 51 include an inner notch 59a which corresponds with one or more stops 60a of the diaphrams 53a to prevent outward movement and hence, to achieve only one-way flow. The stops 60a generally extend along at least a portion of the length of the diaphram, and may be situated along the entire length. It should be apparent that the response of the diaphrams 53, 53a in the preceding embodiments to a predetermined pressure creates a variable clearance in the slots in which the diaphrams are positioned, such that fluid from the ventricle is introduced into the proximal catheter for drainage through the shunt system as previously described.

In FIG. 9, there is illustrated another form of a parallel slit valve of the invention designated as slit valve 50b. Parallel slit valve 50b is similar to the valves of FIGS. 8 and 10, except that the cross-sectional area 58b of the four diaphrams is approximately square, such that inward and outward movement of the diaphrams 53b is possible, an acceptable response in certain situations. Valve 50b can be used with external stops placed opposite diaphrams 58b (not shown) to limit outward movement, and hence, bi-directional flow.

Although each of the embodiments of the proximal parallel slit valves in FIGS. 8, 9 and 10 are described with reference to a single valve, it is within the scope of the invention to employ multiple proximal parallel valves of the type shown in FIGS. 8, 9 and 10, which would provide added flow during drainage of the ventricle, as well as back-up functioning in case of malfunction of one of the valves. A relief valve (not shown) could be provided in one of the valves responsive to a higher opening pressure to serve as a fail safe in the event the other valves become occluded. By being calibrated correctly, the fail safe valve would not allow the intercranial pressure to reach a critical level. The actual construction of the valve diaphrams as herein disclosed is dependent on thickness, elasticity of the diaphram material, width of the diaphram, overall diaphram length for a given shunt material, and the desired operating pressure. One overall advantage of the proximate parallel slit valves as shown in FIGS. 8, 9 and 10, is directed to the fact that no straight reservoir or column fluid of cerebrospinal fluid is formed which could sediment and cause valve malfunction.

Referring to FIGS. 11 and 12, there is illustrated an embodiment of a variable pressure proximal valve of the invention which prevents the risk presently known in shunting of collapsed lateral ventricles occasioned by patients having large ventricles and/or high pressure. The novel features of the variable pressure proximal valve 70 of FIGS. 11 and 12 may be used in conjunction with the proximal slit valves 50 of the type described in connection with FIGS. 8, 9 and 10. In FIGS. 11 and 12, an adjustment sleeve 71, which is movable within the ventricle catheter 72, is placed on either end of the valve diaphrams 50. The sleeve 71, when moved in the appropriate direction, acts to restrict the useable length of the parallel slit valves 50 and, in effect, increases the opening pressure required for valve function. The actuation of the control sleeve 71 is achieved by an elongated rod 74 having one end 75 suitably coupled to a part of the sleeve. The end portion 75 includes a threaded length which engages a threaded tube 75a affixed to a portion of the inner surface of the sleeve 71. It is also within the scope of the invention to orient the threaded tube centrally of the sleeve 71 using webs and the like, if desired. The opposite end 76 of the rod is coupled to a disc assembly 77 in which one or more high strength magnets of cobalt or the like 78 are imbedded in a disc 79 mounted for rotation in a housing 80, coupling the proximal catheter 78 and the distal shunt catheter 81. A corresponding actuator magnet (not shown) is used to rotate the assembly from an external position on the surface of the skin which has the effect of turning the rod and moving the adjustment sleeve 71, because of the action of the threaded end 75 of the rod and the tube 75a to effect changes in the operating pressure of the proximal parallel valve 50.

When used in clinical situations, the variable pressure valve 70 can initially be placed in the most closed position and at approximate intervals, be turned down to decrease the operating pressure of the valve and thereby slowly decreasing the interventricular pressure over a matter of days, weeks or the like. To prevent unwanted rotation of the adjustment assembly 76, rotation stops (not shown) can be installed between the assembly and the housing. These stops would provide a slight impediment to rotation and make a slight clicking sound as the assembly is adjusted. By the use of a stethoscope placed near the housing, these clicks could serve as an indication of desired rotation. Radio-opaque markers could be placed in both the ventricular catheter and the adjustment sleeve so that lateral skull x-rays would indicate position and/or change of position of the adjustment valve.

Referring now to FIGS. 13, 14, and 15, there is illustrated an improved trocar 90 of the invention for inserting a ventricular or peritoneal catheter and for acting as a rigid support guide because the cathter itself is too flexible for unaided insertion. The trocar of the invention includes two elongated members in the form of an inner section 91 and an outer section 92 that perform together the necessary function of inserting the catheter into the correct location within the body. The two sections are in the form of semi-rigid plastic tubes with approximately ¼ to ⅓ of the wall removed from each along an axial direction to form a pair of spaces or slots 93 and 94, respectively. The outer trocar section is provided with a slightly larger diameter than the other section to permit insertion of one of the sections into the other as shown in FIGS. 13 and 14. At the ends of each of the trocar sections 91 and 92 are respective handles 95 and 96 which aid in the positioning and insertion of the trocar during surgery. A small ridge (not shown) on the handle end of the trocar can be provided to keep each section properly aligned with respect to the catheter.

In operation, the trocar sections 91 and 92 are placed around the catheter 97 at the end, with the inner end of the trocar resting against the ridge 98 provided on the end plug 99 of the catheter 97 as shown in FIG. 13. Calibration markings or indicia 100 can be provided on the trocar section 92 to show penetration depth as the surgery proceeds during insertion of a catheter into the body area. After insertion is completed into the body cavity, it is sometimes desirable to test the system patency of the enclosed shunt tubing. To perform this function, the surgeon simply rotates the handle of the trocars in a direction which will align the tube slots 93 and 94 and expose the catheter to the cerebrospinal fluid. If patency of the system is not evident at this point, the trocar can be re-rotated to move it either deeper or pull it outward. Once patency has been assured and catheter location is correct, the outer trocar 92 can be pulled out of the shunt tract and lifted off the catheter. While being semi-rigid, the walls of the trocar sections 91 and 92 can be deformed to permit easy removal. The inner trocar 91 is then pulled back by holding the catheter at the outlet site to insure that the location of the catheter will not deviate. The inner trocar section 91 is then removed from the shunt in the same manner as the outer trocar 92.

In the embodiment shown in FIGS. 14 and 15, the openings or slots 93 or 94 within each of the trocar sections 91 and 92, respectively, are deposed in a straight axial direction. However, the slots can also be in a spiral configuration (not shown) such that both turning of the trocars with respect to each other is more readily accomplished and more fenestrations at the proximal tip will be exposed when the trocars are rotated for patency testing. The proximal end of the trocar 90 can have the openings 93 and 94 which are wider than the rest of the trocar to allow patency testing, but still have a sufficient diameter in the rest of the tube to remain rigid. If desired, the trocar can also be coated with Teflon or the like to lessen the friction between a trocar section and the catheter and/or between the inner and outer trocar sections themselves.

The handles 95 and 96 of the ends of each trocar section 91 and 92 are constructed, so that when turned, one fits under the other at the full rotation point. Thus, for example, the operator would be aware that when the handles are rotated 180° from each other, an indication is made of the insertion position and when the handles are brought together, patency testing can be accomplished.

Referring now to FIG. 16, there is illustrated a variable pressure valve with an anti-syphon device of the invention for use with the above shunting system. The variable pressure valve 110 is similar to the valve described in connection with the embodiment of FIGS. 11 and 12 and includes a bellows 111 disposed within the magnet housing 112 of the variable pressure valve. The magnetic housing includes a disc-like rotator 113 having magnets 113a, similar as shown in FIGS. 11 and 12. The adjustment rod 114 is threadly secured to rotator 113, so that upon its rotation by an actuator magnet (not shown) the sleeve 115 is moved to control the response of valve 110. The anti-syphon bellows 111 is secured in a sealed relationship to rotator 113. The front wall 111a of bellows 111 suports a central sleeve 115 which permits the bellows 111 to move axially on rod 114 as well as to rotate relative thereto. The end of proximal catheter 116 includes a gasket 117 to contact the front wall 111a to terminate or restrict flow when the bellows responds to a negative pressure. The surface area of the bellows 111 is approximately eight times greater than the inner diameter of the proximal catheter 116. By use of the anti-syphon bellows according to the invention, a regulated intercranial pressure can be maintained regardless of the patient's position or movement. Even in the situation where bellows 111 is restricting the flow of the proximal catheter, a pressure of only slightly greater than normal will be required to overcome the pressure differential presented by the catheter syphoning effect.

Referring now to FIGS. 17, 18 and 19, there are illustrated three embodiments of a reduceable pressure slit valve according to the invention for use in a shunt system, such as used in the one piece shunt, although the slit valves herein disclosed are not exclusively limited to use in this system. As was discussed previously, pressure slit valves are typically positioned at the distal end of certain forms of shunt systems. Referring now to FIG. 18, there is illustrated a slit valve 120 of the invention having a plurality of slits 121 through which the fluid may pass in response to the pressure in the system. Such slit valves are normally responsive to either of three preset pressure ranges, i.e., high, medium or low. In most cases, the major difference between shunts to create such differing pressure responses is simply to lengthen the slit, i.e., the longer the slit, then the lower the resultant opening pressure will be.

The valve 120 of FIG. 17 permits the slit 121 having a short length for high pressure application to be quickly modified by the surgeon at the time of surgery to adjust the length of the slit valve from a short slit in its manufactured form to medium or low pressure response in accordance with the needs of the particular patient. In FIG. 17, the pressure limiter includes a pair of blebs 125 which are placed on each of the slits to hold them together at the correct location and block flow through a portion of each of the slits for a high pressure requirement as manufactured. The blebs 125 in FIG. 17 comprise small frangible septums which extends the entire width of the catheter wall 126 and allow flow through only the central portion 127 of the slit. For example, the slits may have the following lengths; for high pressure, 4 millimeters; medium pressure, 5 millimeters; and low pressure, 6 millimeters. Thus, if one of the blebs 125 is broken by the surgeon in each slit 121 at the time of surgery, the slit valve would be adjusted to have a medium pressure response or if both are broken to maximize the length of the slit, then a low pressure response of the slit valve would be present.

Referring to FIG. 18, there is disclosed another embodiment of the reducible pressure slit valve 120a, which is similar to that shown in FIG. 17, except that the blebs 125a are in the form of a small dot positioned at the outer surface of the catheter and only holding that part of the slits together and block flow through a portion of the slits to create a high pressure response. In FIG. 19, another reducible pressure slit valve 120b is shown having small blebs 125b located at the outer wall of the catheter to provide high, low or medium response, but are interconnected with a small film of material that tears when desired. In other situations, heat welds could also be used in place of the blebs to provide adjustability of the length of the slits (not shown). It should be apparent from the description of the embodiments of FIGS. 17, 18 and 19, that one or two of the blebs in one or more slits are broken at the time of surgery. Separation of the blebs, which is material interconnecting the slits, could be accomplished by either a manipulation between the fingers of the surgeon, or with the use of a small blunt tool pulled down the slit and thereby breaking the desired pressure limiter.

Referring now to FIG. 20, there is illustrated a neonatal shunt clip 130 of the invention for use in conjunction with any suitable shunt system. The neonatal shunt clip of the invention is to be used in those patients where the high profile of the regular shunt clip can cause problems with the skin necrosis due to pressure. The clip of the invention is less bulky than the prior art clips, and much easier to insert into the shunt and secure at the time of surgery. The modified clip, as disclosed, is not exclusively used for the neonate, as it can be easily used in the older patient when desired.

The clip 130 includes a curved body portion 131 having an open top 132 and raised edges 133 through which the catheter (not shown) may be disposed. The end of the clip body includes a split retaining ring 134 having a slot 135 to permit insertion of the shunt therethrough. The clips 130 of the invention may be used to anchor both the proximal catheter and the distal catheter. Upon the catheter being attached to the clip, the catheter may be secured against movement by a clamp 140 having a resiliently disposed jaw 141 to grip the catheter. The resiliency of the jaw is achieved by using plastic material which resiliently permits the jaws 141 to be separated and grip the catheter for securement. Suture holes 142 are provided in each of the two jaws to permit the final securement of the clip to the patient's body. Thus, the shunt is simply snapped into the lower portion of the clip and pressed into the holding jaws.

The jaws are both curved and angled so that it holds the shunt in place while at the same time prevents migration of the catheter form its desired location.

Referring now to FIGS. 21 and 22, there is illustrated an embodiment of an improved shunt clip 160 of the type of a construction similar to that typically used in the prior art. In normal shunt systems, access to the interior of the shunt line is limited unless bulky access parts are provided. It is advantageous at times to be able to pass a syringe into the shunt, and aspirate some fluid or to remove some cerebrospinal fluid for testing and the like. The improved shunt clip 160 shown in FIGS. 21 and 22 permits such access because of the presence of a port 161 through the body of the shunt clip. The port is covered by a self healing silicone elastomer 162 or other type of material which seals itself upon being punctured. The lower edge of the plastic extends below the clip body so that when the clip is snapped in place, it seals the space between the shunt and the clip. This water tight seal prevents leakage after a suitable syringe is passed into the shunt for testing and the like. Since the clip is much harder then the center, the clip funnels the syringe directly into the center of the shunt preventing laceration to the wall of the catheter. Since the clip is easily palable, the syringe is simply passed in the center of the clip until fluid is obtained, and the syringe may be removed and the plastic again reseals itself.

While the invention has been described with reference to the preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A catheter assembly for a physiological fluid shunt system comprising:
    catheter means for draining fluid from a source of a patient,
    said catheter means having a first tubular section and a second tubular section, each of said tubular section being adapted to be restrained at an end portion by attachment to the patient's body,
    said first tubular section having an outer diameter less than the outer diameter of said second tubular section,
    at least a position of said first tubular section being concentrically inserted within at least a portion of said second tubular section in spaced relationship to permit relative movement automatically therebetween in response to the application of tensile force to said catheter means as a result of physiological growth of the patient,
    sealing means disposed between said first and second tubular sections to permit said relative movement and prevent the passage of fluid being drained through the space therebetween, said sealing means includes at least one continuous annular gasket member extending between said first and second tubular sections and frictionally contracting one of said first and second tubular sections,
    said at least gasket member includes a one continuous flange member coupled to said first tubular section and extending outward to contact said second tubular section at a peripheral edge portion, said flange member having an outer diameter greater than the inner diameter of said second tubular section to cause said flange member to deflect at said end portion and create sealing contact therewith while permitting relative movement between said first and second tubular members in response to physiological growth of the patient,
    said sealing contact occurring at an outer region of said flange member adjacent said edge portion for attaining enhanced sealing contact and preventing relative movement except as a result of the forces generated by the patient's physiological growth.

2. The catheter assembly according to claim 1 wherein said at least one continuous flange member includes a plurality of spaced flange members, said flange members possess a diameter greater than said inner diameter of said second tubular member.

3. The catheter assembly according to claim 1 wherein said at least one gasket member is flexible.

4. The catheter assembly according to claim 1 wherein said sealing member permits relative movement in one direction in response to growth of the patient and prevents movement in the opposite direction.

* * * * *